(12) United States Patent
Lin

(10) Patent No.: US 11,286,572 B2
(45) Date of Patent: Mar. 29, 2022

(54) GAS GENERATOR

(71) Applicant: Hsin Yung Lin, Shanghai (CN)

(72) Inventor: Hsin Yung Lin, Shanghai (CN)

( * ) Notice: Subject to any disclaimer, the term of this patent is extended or adjusted under 35 U.S.C. 154(b) by 0 days.

(21) Appl. No.: 15/389,395

(22) Filed: Dec. 22, 2016

(65) Prior Publication Data

US 2018/0320275 A1 Nov. 8, 2018

(30) Foreign Application Priority Data

Dec. 22, 2015 (TW) ................................ 104143082

(51) Int. Cl.
*C25B 1/04* (2021.01)
*A61M 16/10* (2006.01)
(Continued)

(52) U.S. Cl.
CPC ............ *C25B 1/04* (2013.01); *A61M 16/0087* (2013.01); *A61M 16/10* (2013.01); *A61M 16/1005* (2014.02); *C25B 9/67* (2021.01); *C25B 9/73* (2021.01); *A61M 16/12* (2013.01); *A61M 16/14* (2013.01); *A61M 2016/1035* (2013.01); *A61M 2202/0208* (2013.01); *A61M 2205/07* (2013.01); *A61M 2205/18* (2013.01);
(Continued)

(58) Field of Classification Search
CPC ......... C25B 1/02–12; C25B 1/04; C25B 9/67; C25B 15/021; A61M 16/1005; A61M 16/12; A61M 2202/0208; A61M 2205/18; A61M 2205/3327; Y02E 60/366
See application file for complete search history.

(56) References Cited

U.S. PATENT DOCUMENTS

2006/0231386 A1* 10/2006 Kanematsu ............... C25B 1/10
 204/252
2007/0251830 A1* 11/2007 Conrad ..................... C25B 1/02
 205/508
(Continued)

FOREIGN PATENT DOCUMENTS

CA 2854390 A1 * 12/2014 ............ A61M 16/14
CN 102191511 A 9/2011
(Continued)

OTHER PUBLICATIONS

Office Action, Chinese Application No. 201510968339.5, dated Apr. 27, 2018, 14 pages.

*Primary Examiner* — Ciel P Contreras
(74) *Attorney, Agent, or Firm* — Rosenberg, Klein & Lee

(57) ABSTRACT

The preferred embodiment of the invention provides a gas generator comprising an ion membrane electrolytic cell and an atomized/volatile gas mixing tank. The ion membrane electrolytic cell comprises an ion exchange membrane, a cathode chamber and an anode chamber. An anode electrode is set in the anode chamber, and a cathode electrode is set in the cathode chamber. The ion exchange membrane is set between the anode chamber and the anode chamber. When water is electrolyzed by the ion membrane electrolytic cell, oxygen is generated by the anode electrode and hydrogen is generated by the cathode electrode. The atomized/volatile gas mixing tank coupled to the ion membrane electrolytic cell accepts the hydrogen generated from the ion membrane electrolytic cell and generates an atomized gas to mix with the hydrogen for generating a healthy gas.

2 Claims, 6 Drawing Sheets

(51) Int. Cl.
*A61M 16/00* (2006.01)
*C25B 9/73* (2021.01)
*C25B 9/67* (2021.01)
*A61M 16/12* (2006.01)
*A61M 16/14* (2006.01)

(52) U.S. Cl.
CPC . *A61M 2205/3327* (2013.01); *A61M 2205/75* (2013.01); *A61M 2205/8231* (2013.01); *Y02E 60/36* (2013.01)

(56) References Cited

U.S. PATENT DOCUMENTS

| 2008/0264780 | A1* | 10/2008 | Kato | C25B 1/04 204/252 |
| 2010/0276299 | A1* | 11/2010 | Kelly | C25B 9/00 205/628 |
| 2012/0090989 | A1* | 4/2012 | Haryu | C25B 1/04 204/237 |
| 2012/0209434 | A1* | 8/2012 | Kurashina | C25B 1/12 700/273 |
| 2012/0222955 | A1* | 9/2012 | Takeuchi | C25B 15/08 204/257 |
| 2013/0206586 | A1* | 8/2013 | Lin | C25B 15/02 204/228.2 |
| 2014/0048067 | A1* | 2/2014 | McGill | A61M 16/10 128/203.29 |
| 2015/0292091 | A1* | 10/2015 | Satoh | C25B 1/04 204/265 |

FOREIGN PATENT DOCUMENTS

| CN | 203291354 U | 11/2013 |
| CN | 103785091 A | 5/2014 |
| CN | 104379812 A | 2/2015 |
| CN | 204409932 U | 6/2015 |
| TW | M411434 U | 9/2011 |

* cited by examiner

GAS GENERATOR

PRIORITY CLAIM

This non-provisional application claims priority under 35 U.S.C. § 119(a) to Patent Application No. 104143082 filed in Taiwan on Dec. 22, 2015, the entire contents of which is hereby incorporated by reference as if fully set forth herein.

This application also claims priority under 35 U.S.C. § 119(a) to U.S. patent application Ser. No. 14/22,338 entitled GAS GENERATOR FOR HEALTH USE filed Mar. 27, 2014; U.S. patent application Ser. No. 14/227,703 entitled ANTI-EXPLOSION GAS GENERATOR FOR HEALTH USE filed Mar. 27, 2014; U.S. patent application Ser. No. 14/227,844 entitled LIQUID-GAS CYCLING SYSTEM FOR ELECTROLYTIC TANK OF HEALTH GAS GENERATOR filed Mar. 27, 2014; U.S. patent application Ser. No. 14/508,383 entitled A GAS VENDING SYSTEM FOR HEALTH APPLICATION filed Oct. 7, 2014; U.S. patent application Ser. No. 14/508,656 entitled A GAS GENERATOR FOR HEALTH USE HAVING SECURITY SYSTEM filed Oct. 7, 2014; U.S. patent application Ser. No. 14/553,002 entitled A GAS GENERATOR filed Nov. 25, 2014; U.S. patent application Ser. No. 14/553,132 entitled MODULARIZED HEALTH GAS GENERATOR filed Nov. 25, 2014; U.S. patent application Ser. No. 14/664,465 entitled INHALATION-TYPE PHARMACEUTICAL COMPOSITION FOR THE TREATMENT OF PARKINSON'S DISEASE AND PREPARATION METHOD THEREOF filed Mar. 20, 2015; U.S. patent application Ser. No. 14/664,483 entitled INHALATION-TYPE PHARMACEUTICAL COMPOSITION FOR THE TREATMENT OF ALZHEIMER'S DISEASE AND PREPARATION METHOD THEREOF filed Mar. 20, 2015; U.S. patent application Ser. No. 14/664,491 entitled INHALATION-TYPE PHARMACEUTICAL COMPOSITION FOR THE TREATMENT OF HEART DISEASE AND PREPARATION METHOD THEREOF filed Mar. 20, 2015; U.S. patent application Ser. No. 14/664,508 entitled INHALATION-TYPE PHARMACEUTICAL COMPOSITION FOR THE TREATMENT OF ARTHRITIS AND PREPARATION METHOD THEREOF filed Mar. 20, 2015; U.S. patent application Ser. No. 14/664,522 entitled INHALATION-TYPE PHARMACEUTICAL COMPOSITION FOR THE TREATMENT OF GOUT AND PREPARATION METHOD THEREOF filed Mar. 20, 2015; U.S. patent application Ser. No. 14/665,989 entitled INHALATION-TYPE PHARMACEUTICAL COMPOSITION FOR THE TREATMENT OF KIDNEY DISEASE AND PREPARATION METHOD THEREOF filed Mar. 23, 2015; U.S. patent application Ser. No. 14/666,037 entitled INHALATION-TYPE PHARMACEUTICAL COMPOSITION FOR THE TREATMENT OF LUNG CANCER AND PREPARATION METHOD THEREOF filed Mar. 23, 2015; U.S. patent application Ser. No. 14/666,069 entitled INHALATION-TYPE PHARMACEUTICAL COMPOSITION FOR THE TREATMENT OF HYPERTENSION AND PREPARATION METHOD THEREOF filed Mar. 23, 2015; U.S. patent application Ser. No. 14/666,097 entitled INHALATION-TYPE PHARMACEUTICAL COMPOSITION FOR THE TREATMENT OF DIABETES AND PREPARATION METHOD THEREOF filed Mar. 23, 2015; U.S. patent application Ser. No. 14/828,765 entitled LIQUID ELECTROLYTIC DEVICE filed Aug. 18, 2015; U.S. patent application Ser. No. 14/875,629 entitled A GAS GENERATOR filed Oct. 5, 2015; U.S. patent application Ser. No. 15/064,516 entitled HYDROGEN RICH WATER GENERATOR filed Mar. 8, 2016; U.S. patent application Ser. No. 15/064,558 entitled A GAS GENERATOR filed Mar. 8, 2016; and U.S. patent application Ser. No. 15/297,344 entitled BREATHING MASK AND GAS PROVIDING DEVICE filed Oct. 19, 2016; the entire contents of these applications is hereby incorporated by reference as if fully set forth herein.

FIELD OF THE INVENTION

The present invention relates to a gas generator.

BACKGROUND OF THE INVENTION

People are always paying a great deal of attention on health developments. Many developments in medical technology are often targeted on treating diseases and prolonging human life. However, most of the treatments in the past are passive, which means that they only treat the disease when the disease occurs. These methods include operations, medications, radiation therapies, chronic diseases care, rehabilitations, corrective therapies, or even medical treatments for cancers. But in recent years, much of the research from medical experts are gradually moving towards preventive medical methods, such as research on healthy food, screening and preventing inherited diseases, which actively prevents diseases from occurring in the future. Because of the focus on prolonging human life, many anti-aging and anti-oxidation technologies including skin care products and anti-oxidation food/medicine are gradually being developed and have become increasingly popular to the general public.

Studies have found that there are instable oxygen species (O+), also known as free radicals, in the human body. The free radicals which are usually generated due to diseases, diet, environment and one's lifestyle can be excreted in the form of water by reacting with inhaled hydrogen. With this method, the amount of free radicals in the human body can be reduced, thereby restoring the body condition from an acidic state to an alkaline state, achieving an anti-oxidation, anti-aging and beauty health effect, and even eliminating chronic diseases. Furthermore, there are also clinical experiments showing that patients who need to inhale a high concentration of oxygen for an extended period of time would experience lung damage, but that the damage could be ameliorated by inhaling hydrogen.

In addition to health uses, the application of hydrogen-oxygen gas also can create hydrogen-oxygen fire to heat or burn, or clean up the carbon accumulated in engine as well. Generally, hydrogen-oxygen gas is generated through electrolyzing liquid water. However, it's easy to generate high temperature in the electrolyzing process, which causes the efficiency of electrolyzing to be decreased and energy consumption problems. Moreover, in order to avoid hydrogen explosions, air-cooling type hydrogen-oxygen electrolysis tank are usually used (by utilizing fan to cool down). However, if the fan malfunctions, the temperature of the electrolysis tank will be raised, which increases the risk of hydrogen explosions.

BACKGROUND OF THE INVENTION

Embodiments of the present invention provides a gas generator, comprising an ion membrane electrolytic cell and an atomized/volatile gas mixing tank. The ion membrane electrolytic cell comprises an ion exchange membrane, a cathode chamber and an anode chamber. An anode electrode is set in the anode chamber, and a cathode electrode is set in the cathode chamber. The ion exchange membrane is set between the cathode chamber and the anode chamber. Wherein when the water is electrolyzed by the ion membrane electrolytic cell, oxygen is generated by the anode electrode, and hydrogen is generated by the cathode electrode. The atomized/volatile gas mixing tank is connected with the ion membrane electrolytic cell, and the atomized/volatile gas mixing tank receives hydrogen generated by the ion membrane electrolytic cell. The atomized/volatile gas mixing tank generates an atomized gas to mix with hydrogen to form a healthy gas, wherein the atomized gas is able to be selected from a group consisting of volatile oil, vaporized medicinal liquid, water vapor and a combination thereof.

The ion membrane electrolytic cell can further comprise a gas tube, and the gas tube is connected with the cathode chamber. The gas generator further comprises a gas pump for receiving air. The gas pump inputs the air to the cathode chamber by the gas tube to decrease the concentration of hydrogen and form the hydrogen mixed gas. The atomized/volatile gas mixing tank receives the hydrogen mixed gas mixing with the atomized gas to form a healthy gas.

The ion membrane electrolytic cell can further comprise a hydrogen tube. The hydrogen tube the hydrogen tube is connected with the cathode chamber to output the hydrogen mixed gas from the cathode chamber. The gas generator can further comprise a hydrogen concentration detector and a processor. The hydrogen concentration detector is connected with the hydrogen tube to detect the concentration of hydrogen in the hydrogen mixed gas, and an alarm signal is generated when the concentration of hydrogen detected by the hydrogen concentration detector is higher than a predetermined value. A processor is coupled with the hydrogen concentration detector and the ion membrane electrolytic cell, and a stop signal is generated to stop the operation of the ion membrane electrolytic cell when the alarm signal is received by the hydrogen concentration detector, wherein the predetermined value is 3.5% which is the gas volume concentration of hydrogen in the hydrogen mixed gas.

The ion membrane electrolytic cell can further comprise a hydrogen tube, and the hydrogen tube is connected with the cathode chamber to output hydrogen in the cathode chamber. The gas generator can further comprise a gas-water separator which is set between the ion membrane electrolytic cell and the atomized/volatile gas mixing tank. The gas-water separator receives hydrogen to separate hydrogen from water, wherein the atomized gas is generated and mixed with hydrogen which is separated from water to form the healthy gas after the atomized/volatile gas mixing tank receives hydrogen separated from water.

The gas generator can further comprise a hydrogen concentration detector and a processor. The hydrogen concentration detector connected with the gas-water separator detects the concentration of hydrogen which is separated from water. An alarm signal is generated when the concentration of hydrogen detected by the hydrogen concentration detector is higher than a predetermined value. A processor is coupled with the hydrogen concentration detector, and the ion membrane electrolytic cell generates a stop signal to stop the operation of the ion membrane electrolytic cell when the alarm signal is received.

The gas generator can further comprise an atomized/volatile gas mixing tank. The atomized/volatile gas mixing tank is connected with the ion membrane electrolytic cell, and the atomized/volatile gas mixing tank receives oxygen generated by the ion membrane electrolytic cell. The atomized/volatile gas mixing tank generates an atomized gas to mix with hydrogen to form a healthy gas for the user to inhale, wherein the atomized gas is able to be selected from a group consisting of volatile oil, vaporized medicinal liquid, water vapor or a combination thereof.

The gas generator can further comprise a water tank accommodating water. The water tank is connected with the ion membrane electrolytic cell for recharging water into the anode chamber and the cathode chamber.

The ion membrane electrolytic cell can further comprise an oxygen tube. The oxygen tube is connected with the anode chamber. The ion membrane electrolytic cell inputs the oxygen generated by the anode chamber into the water tank through the oxygen tube and discharged from the water tank.

The ion exchange membrane comprises an ion exchange membrane body, an anode catalyst layer and a cathode catalyst layer. The anode catalyst layer and the cathode catalyst layer are respectively disposed in the anode chamber and cathode chamber, and two sides of the ion exchange membrane body. The anode catalyst layer is selected from a group consisting of Pt, Ir, Pd, the alloy powder of Pt, carbon or any combination of thereof, the cathode catalyst layer is selected from a group consisting of Pt, Ir, Pd, the alloy powder of Pt, carbon or any combination of thereof, and the ion exchange membrane body is a Nafion membrane.

The cathode electrode can comprise a cathode electrode plate and a cathode collector plate. The anode electrode can comprise an anode electrode plate and an anode collector plate. The cathode electrode plate is set between the ion exchange membrane and the cathode collector plate. The anode electrode plate is set between the ion exchange membrane and the anode collector plate. The cathode collector plate and the anode collector plate are connected with an external power source.

The gas generator can further comprise two fins, wherein the two fins is set on the outsides of the ion membrane electrolytic cell; a fin is close to the cathode collector plate, and the other fin is close to the anode collector plate.

Embodiments of the present invention further provides another gas generator which comprises an ion membrane electrolytic cell and a gas pump. The ion membrane electrolytic cell comprises an ion exchange membrane, a cathode chamber and an anode chamber. An anode electrode is set in the anode chamber, and a cathode electrode is set in the cathode chamber. The ion exchange membrane is set between the cathode chamber and the anode chamber. The ion membrane electrolytic cell further comprises a gas tube connected with the cathode chamber. Wherein oxygen is generated by the anode electrode, and hydrogen is generated by the cathode electrode when the ion membrane electrolytic cell electrolyzing water. The gas pump receives air, and the gas pump inputs air into the cathode chamber to decrease the concentration of hydrogen in the cathode chamber to form a hydrogen mixed gas.

To summarize, the ion membrane electrolytic cell used in the gas generator of embodiments of the present invention can solve the problems of the familiar basic cell gas concerning the corrosion of the tank, the environmental pollution and the chance to inhale the gas with electrolyte because the filter has some problems. The gas generator of embodiments of the present invention can receive air from the outside to decrease the concentration of hydrogen in the cathode chamber to make the ion membrane electrolytic cell output the hydrogen with low concentration to decrease the chance of gas explosion and improve the security.

The optional advantages and spirits of embodiments of the invention may be understood by the following recitations together with the appended drawings.

BRIEF DESCRIPTION OF THE DRAWINGS

Preferred and alternative examples of the present invention are described in detail below with reference to the following drawings.

The optional advantages, spirits and features of the present invention will be explained and discussed with embodiments and figures as follows.

DETAILED DESCRIPTION OF THE PREFERRED EMBODIMENT

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Figure 1A:
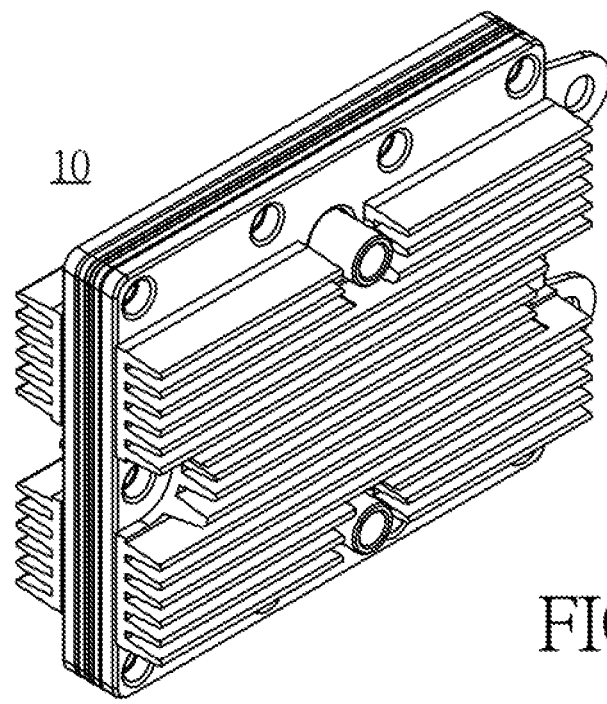
FIGS. 1A and 1B show three-quarters perspective views of the ion membrane electrolytic cell of the present invention in the embodiment.
Figure 1B:
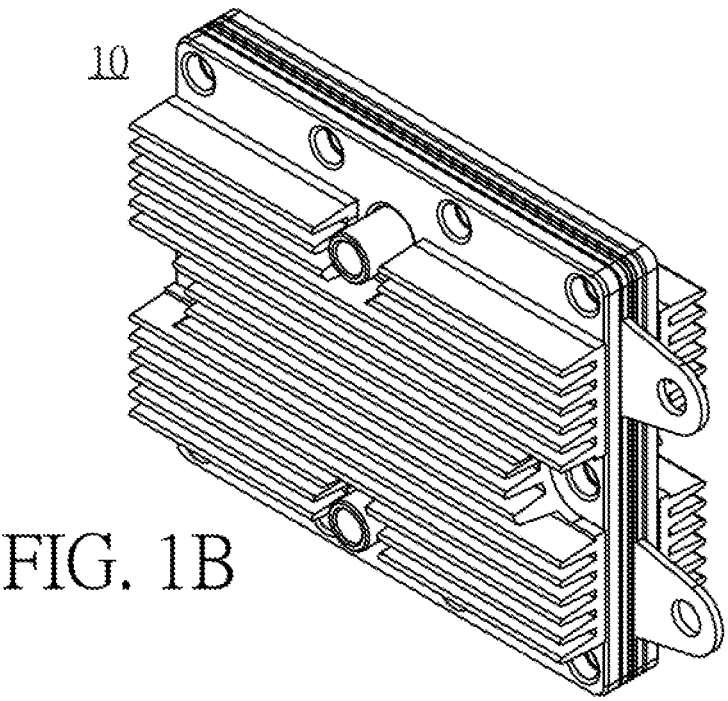
Figure 5:
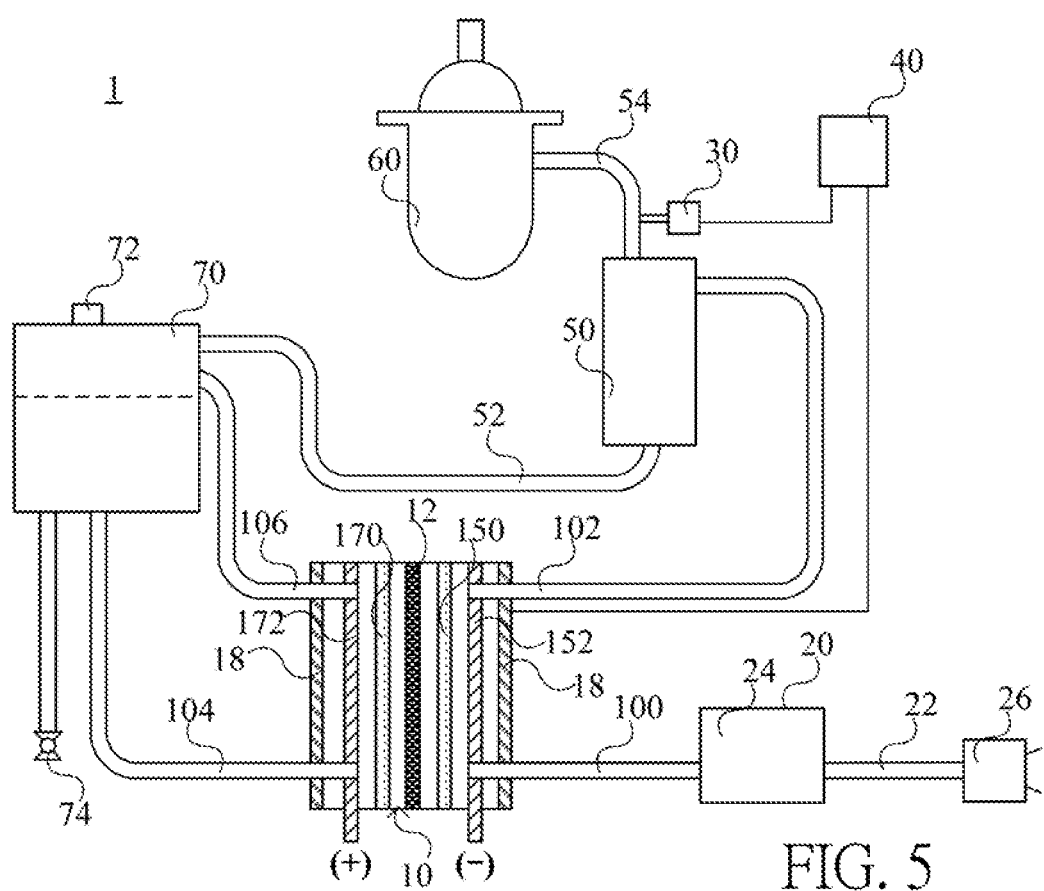
FIG. 5 shows a diagram of the gas generator of the present invention in an embodiment.

Please refer to FIG. 1 and FIG. 5. FIG. 1 shows the diagram of the ion membrane electrolytic cell of the present invention in the embodiment. FIG. 5 shows the diagram of the gas generator of the present invention in an embodiment. The gas generator 1 of the present invention comprises an ion membrane electrolytic cell 10 and an atomized/volatile gas mixing tank 60. An ion membrane electrolytic cell 10 generates hydrogen by electrolyzing water. The atomized/volatile gas mixing tank 60 connected with the ion membrane electrolytic cell 10 can receive hydrogen generated by the ion membrane electrolytic cell 10. In an embodiment, water can be the DI water, but not limited to it, which can generate hydrogen with high concentration. In practice, water is able to be any kind of water that a user can get easily. The atomized/volatile gas mixing tank 60 generates the atomized gas to mix with hydrogen to form a healthy gas, wherein the atomized gas is able to be selected from a group consisting of volatile oil, vaporized medicinal liquid, water vapor or a combination thereof.

Figure 2:
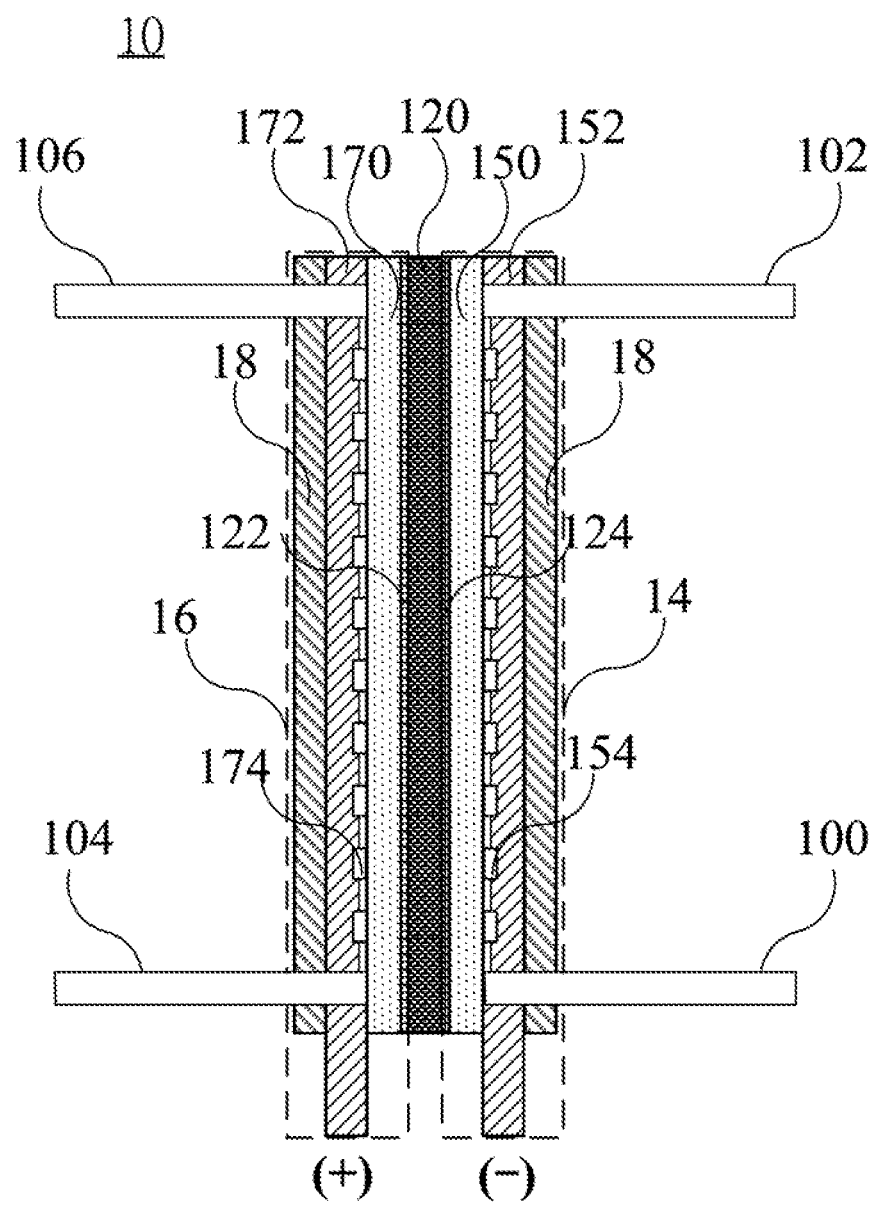
FIG. 2 shows a sectional view of the ion membrane electrolytic cell of the present invention in an embodiment.
Figure 3A:
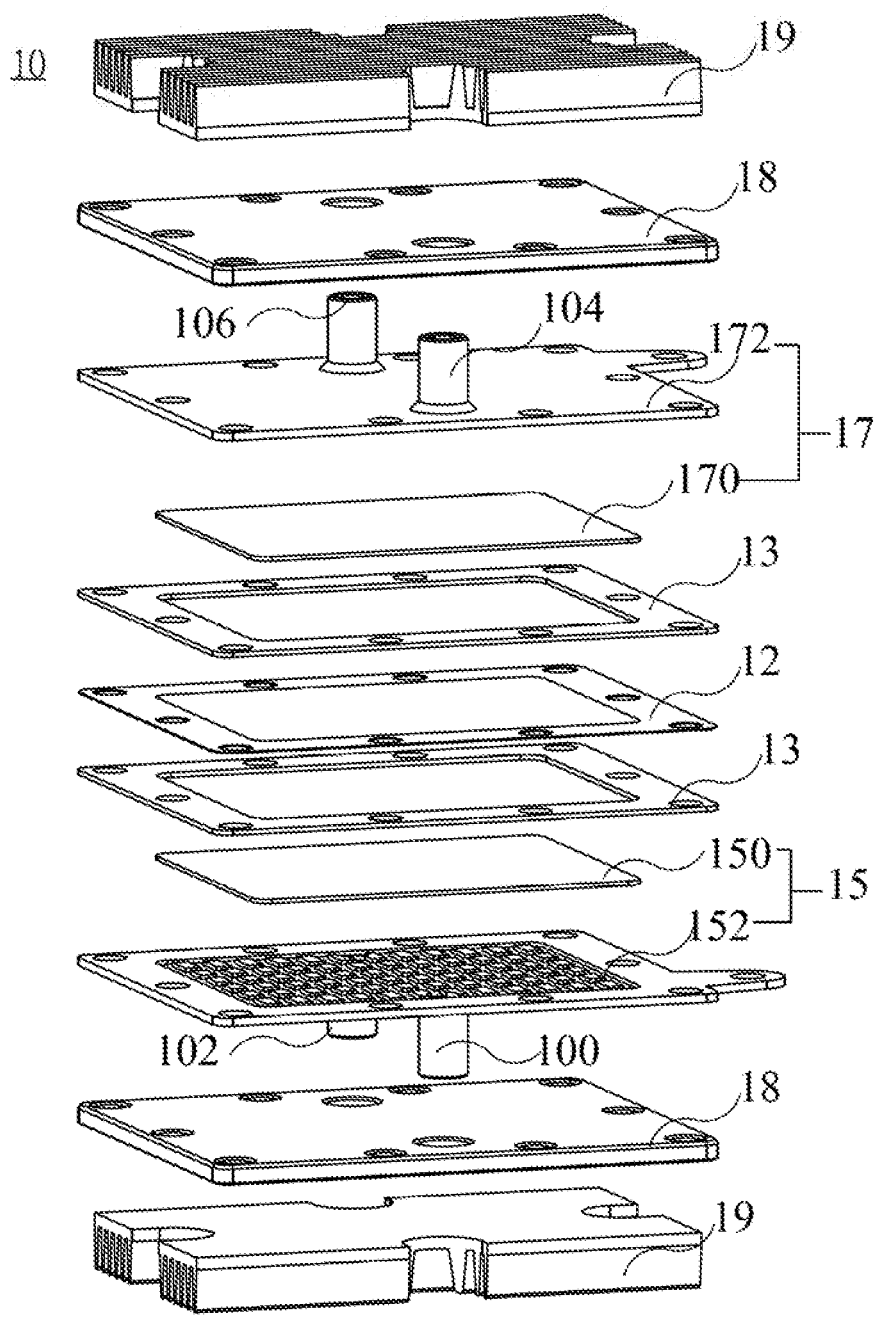
FIGS. 3A and 3B show exploded views of the ion membrane electrolytic cell of the present invention shown in FIG. 1A in an embodiment with different angles.
Figure 3B:
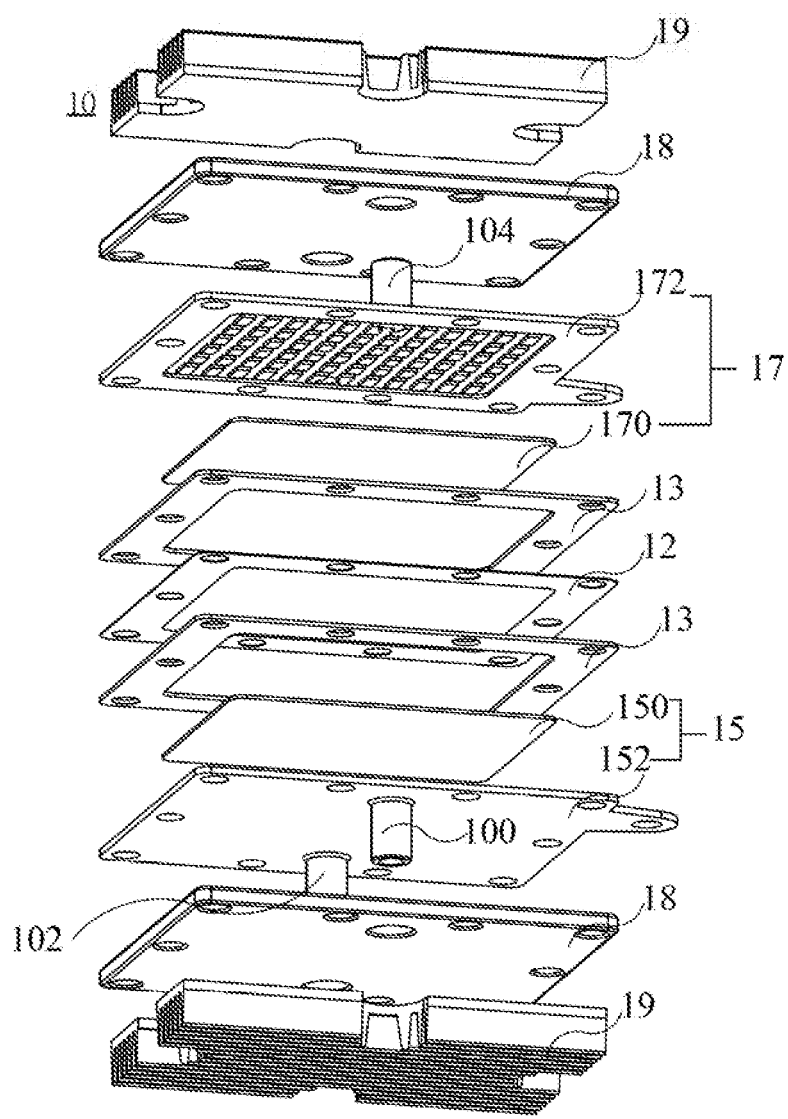

Then, please refer to FIG. 2, FIG. 3A and FIG. 3B. FIG. 2 shows the sectional view of the ion membrane electrolytic cell of the present invention in an embodiment. FIG. 3A and FIG. 3B show the exploded view of the ion membrane electrolytic cell of the present invention shown in FIG. 1A in an embodiment with the different angels. The ion membrane electrolytic cell 10 comprises an ion exchange membrane 12, a cathode chamber 14 and an anode chamber 16. The cathode electrode 15 is set in the cathode chamber 14 shown in FIG. 3A. The anode electrode 17 is set in the anode chamber 16 shown in FIG. 3A. The ion exchange membrane 12 is set between the anode chamber 16 and the cathode chamber 14. Wherein oxygen is generated by the anode electrode 16 and hydrogen is generated by the cathode electrode 14 when the ion membrane electrolytic cell 10 electrolyzes water. Please refer to FIG. 2, the anode chamber 16 and the cathode chamber 14 are respectively set at two sides of the ion exchange membrane 12. To show the relative locations of the anode chamber 16 and the cathode chamber 14 more clearly, they are drawn in dotted line to show their locations. In an embodiment, the anode chamber 16 accommodates water, and water in the anode chamber 16 can penetrate into the cathode chamber 14 through the ion membrane. In another embodiment, the anode chamber 16 and the cathode chamber 14 can accommodate water at the same time. The anode electrode can electrolyze water to generate hydrogen ion and oxygen. The hydrogen ion can penetrate through the ion exchange membrane 12 to the cathode chamber 14, and hydrogen is formed on the cathode electrode 15 after getting the electrode. In practice, hydrogen can be generated, but not limited to, on the catalyst layer; hydrogen can also be generated on the electrode plate or between the ion membrane and the electrode plate. Thereof, the ion membrane electrolytic cell 10 solves the problems the familiar basic cell has. The problems are the corrosion of the tank, the environmental pollution and the chance to inhale the gas with electrolyte because the filter has some problems.

Please refer to FIG. 2. The ion exchange membrane 12 comprises an ion exchange membrane body 120, the anode catalyst layer 122 and the cathode catalyst layer 124. The ion exchange membrane body 120 can be an ion exchange membrane. It is better for the ion exchange membrane body to be a Nafion membrane. The anode catalyst layer 122 and the cathode catalyst layer 124 can be selected from a group consisting of Pt, Ir, Pd, the alloy powder of Pt, carbon or any combination of thereof. In an embodiment, the material of the anode catalyst layer 122 or the cathode catalyst layer 124 is able to be slurry which is disposed on two sides of the ion membrane to form the anode catalyst layer 122 and the cathode catalyst layer 124.

Please refer to FIG. 2. The cathode electrode 15 comprises a cathode electrode plate 150 and a cathode collector plate 152. The anode electrode 17 comprises an anode electrode plate 170 and an anode collector plate 172. In an embodiment, the electrode plate can be a titanium powder die casted plate, and the conductive plate can be titanium. However, the material and the forming method of the electrode plate and the conductive plate are not limited to those mentioned above. Please refer to FIG. 2. In an embodiment, the cathode electrode plate 150 can be set between the ion exchange membrane 12 and the cathode collector plate 152, and the anode electrode plate 170 can be set between the ion exchange membrane 12 and anode collector plate 172. The ion membrane electrolytic cell 10 can be connected with an external power source by the cathode collector plate 152 and the anode collector plate 172. In an embodiment, the anode collector plate 172 shown in FIG. 3B and the cathode collector plate 152 shown in FIG. 3A respectively have runners. When the conductive plate is piled with the relative electrode plate, the plurality of the chamber 174 and 154 shown in FIG. 2 is formed between the anode chamber 16 and the cathode chamber 14. The chamber 174 and 154 can let gas and water flow through it.

Please refer to FIG. 3A and FIG. 3B. FIG. 3A and FIG. 3B show the exploded view of the ion membrane electrolytic cell of the present invention shown in FIG. 1A in an embodiment with the different angels. In an embodiment, the ion membrane electrolytic cell 10 comprises an anode collector plate 172, an anode electrode plate 170, an ion exchange membrane 12, a cathode electrode plate 150 and a cathode collector plate 152, wherein the ion membrane electrolytic cell 10 can be assembled by following the sequence shown in FIG. 3A and FIG. 3B.

The ion membrane electrolytic cell 10 can further comprises an electrode plate sealing gasket 13. In an embodiment, the electrode plate sealing gasket 13 can surround the electrode plate to get the effects such as insulation and airtight, wherein the material of the sealing gasket 13 can be silicon gel. However, the material and setting method of the electrode plate sealing gasket 13 is not limited to those mentioned above. In practice, the material and setting method of the electrode plate sealing gasket 13 can be any kinds of material and setting methods which can get the effects like insulation and airtight.

The ion membrane electrolytic cell 10 can further comprise two platens 18. In an embodiment, after the anode collector plate 172, the anode electrode plate 170, the ion exchange membrane 12, the cathode electrode plate 150 and the cathode collector plate 152 are assembled, the two platens 18 can respectively be set on the outside to fix and isolate, for protecting the whole ion membrane electrolytic cell 10, wherein the plate 18 can be stainless steel.

Figure 4A:
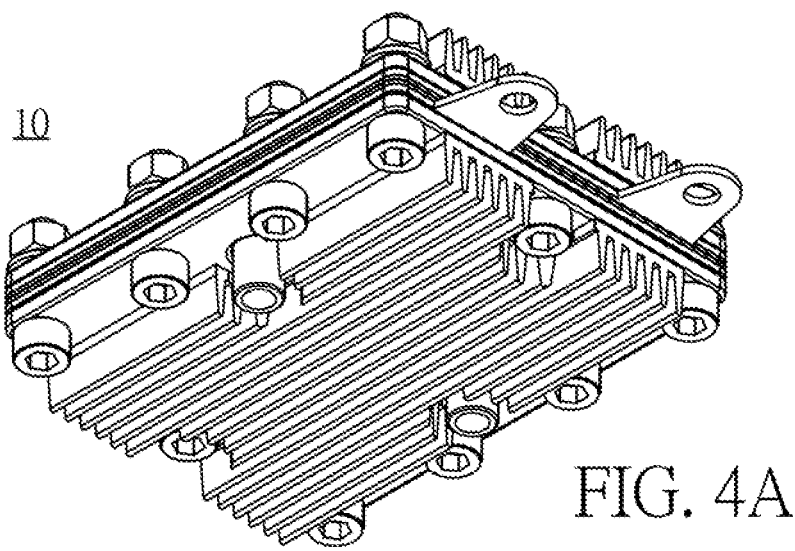
FIGS. 4A and 4B show the ion membrane electrolytic cell of the present invention shown in FIG. 1A locked by the locked element.
Figure 4B:
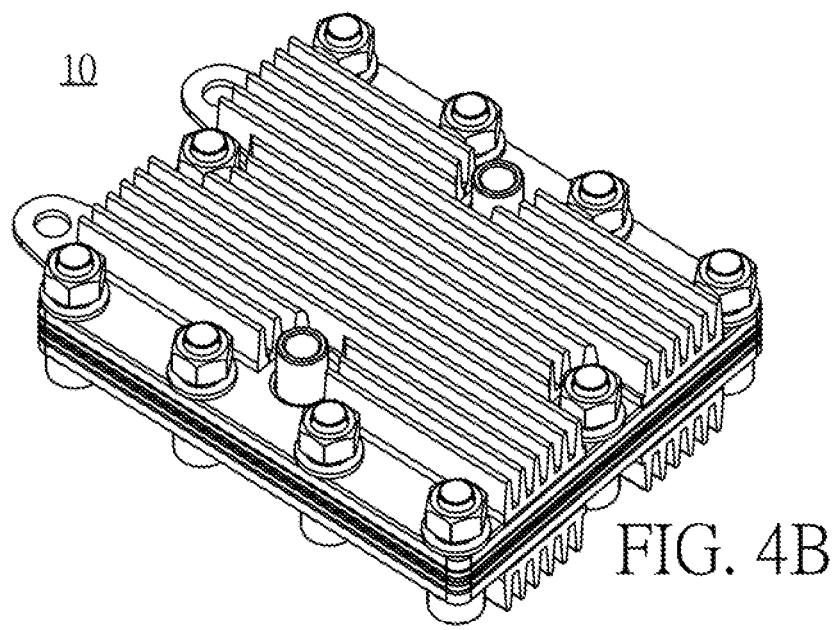

Please refer to FIG. 4A to FIG. 4B. FIG. 4A and FIG. 4B show the ion membrane electrolytic cell of the present invention shown in FIG. 1A locked by the locked element. In an embodiment, after the ion membrane electrolytic cell 10 is assembled, the ion membrane electrolytic cell can be locked by the locked element. However, the amount, type and the method of how to lock are not limited to that mentioned above.

The gas generator 1 can further comprise two fins 19, and the two fins are set on the outside of the ion membrane electrolytic cell 10. One fin is close to the cathode collector plate 152, and the other fin is close to the anode collector plate 172 to release the heat for decreasing the temperature of the ion membrane electrolytic cell 10. As the structure of the ion membrane electrolytic cell 10 is mentioned above, it is not going to be elaborated again. Please refer to FIG. 1A, FIG. 1B, FIG. 3A and FIG. 3B; in an embodiment, a fin can be set on the platen 18 which is close to the cathode collector plate 152, and the other fin can be set on the platen 18 which is close to the cathode collector plate 172. The amount, size, location, design of the fin is not limited to the diagram shown in FIG. 1A to FIG. 3B, and those are able to be adjusted in practice.

Please refer to FIG. 5. FIG. 5 shows the diagram of the gas generator of the present invention in an embodiment. To make the ion membrane electrolytic cell 10 shown in FIG. 5 more clearly, there is a distance among the platen 18, the anode collector plate 172, the anode electrode plate 170, the ion exchange membrane 12, the cathode electrode plate 150, the cathode collector plate 152 and the platen 18. In practice, the elements mentioned above can be assembled.

The gas generator 1 further comprises the hydrogen concentration detector 30 and the processor 40. The ion membrane electrolytic cell 10 further comprises the hydrogen tube 102 which connects the cathode chamber 14 and the atomized/volatile gas mixing tank 60 to input hydrogen in the cathode chamber 14 into the atomized/volatile gas mixing tank 60. In an embodiment, the hydrogen concentration detector 30 can be connected with the hydrogen tube 102 which is also connected with the cathode chamber 14 to detect the concentration of hydrogen in the hydrogen which is outputted from the cathode chamber 14. And the processor 40 can be separately connected with the hydrogen concentration detector 30 and the ion membrane electrolytic cell 10. Wherein the hydrogen can be the hydrogen generated by electrolyzing water by the ion membrane electrolytic cell 10. When the hydrogen concentration detector 30 detects that the concentration of the hydrogen is higher than the predetermined value, the alarm signal is generated, and the processor 40 receives the alarm signal and generates the stop signal to stop the ion membrane electrolytic cell 10, and avoids the gas explosion when the concentration of hydrogen is too high to improve the security. Because the structure of the ion membrane electrolytic cell 10 is already mentioned, it will not be elaborated herein. Please refer to FIG. 3A; in an embodiment, the hydrogen tube 102 can penetrate through the cathode collector plate 152 to connect with the cathode chamber 14 and the outside. The location of the hydrogen tube 102 and the connected method of the hydrogen tube 102 and the cathode chamber 14 are not limited to FIG. 3A. The hydrogen tube 102 can be set on the ion exchange membrane 12, just like the diagram of FIG. 5, or any structure connecting the cathode chamber 14 and the outside.

The gas generator 1 can further comprise a gas pump 20 to receive air. The ion membrane electrolytic cell 10 can further comprise a gas tube 100, and the gas tube 100 can connect the cathode chamber 14 and the outside. Please refer to FIG. 3A; in an embodiment, the gas tube 100 penetrates through the cathode collector plate 152 to connect the cathode chamber 14 and the outside. The location of the gas tube 100 and the connected method of the cathode chamber 14 are not limited to the diagram. The gas tube 100 can be set under the ion exchange membrane 12 shown in FIG. 2 and FIG. 5 or any location which can connect the cathode chamber 14 and the outside. The gas pump 20 can input air into the cathode chamber 14 by the gas tube 100 to decrease the concentration of hydrogen in the cathode chamber 14 to generate the hydrogen mixed gas. In an embodiment, the gas pump 20 can comprise a gas suction tube 22 and the pump 24. The gas suction tube 22 is connected with the outside to receive air outsides. The pump 24 is set between the gas suction tube 22 and the gas tube 100. The pump 24 can connect with the cathode chamber 14 of the ion membrane electrolytic cell 10 by the gas tube 100. By the pump 24, the gas suction tube 22 can receive air from the outside and input air into the cathode chamber 14 to decrease the concentration of hydrogen in the cathode chamber 14 to generate the hydrogen mixed gas. In an embodiment, the atomized/volatile gas mixing tank 60 is connected with the ion membrane electrolytic cell 10 to receive the hydrogen mixed gas to mix with the atomized gas to form the healthy gas, wherein the hydrogen mixed gas can input air from the outside into the cathode chamber 14 by operating the gas pump 20 to decrease the concentration of hydrogen in the cathode chamber 14 to generate the hydrogen mixed gas. In an embodiment, the gas volume concentration of hydrogen in the hydrogen mixed gas can be lower than 3.5%. Accordingly, the possibility of gas explosion caused by the high concentration of hydrogen is decreased and the security is improved because the ion membrane electrolytic cell 10 outputs hydrogen with low concentration. The gas volume concentration is not limited to it. In practice, the concentration of hydrogen is able to be changed according to the requirement of users.

The gas pump 20 can further comprise a gas filter 26 for filtering air from the outside. The gas filter 26 can be connected with the pump 24 by the gas suction tube 22. By operating the pump 24, the gas suction tube 22 can input the filtered gas filtered by the gas filter 26 into the cathode chamber 14 to decrease the concentration of hydrogen in the cathode chamber 14 to generate the hydrogen mixed gas. In an embodiment, the atomized/volatile gas mixing tank 60 is connected with the ion membrane electrolytic cell 10 to receive the hydrogen mixed gas and mix the hydrogen mixed gas with the atomized gas to form the healthy gas, wherein the hydrogen mixed gas is generated by the gas filter 26 filtering the gas and introducing the gas into the cathode chamber 14 to decrease the concentration of hydrogen in the cathode chamber 14.

The gas generator 1 can further comprise the hydrogen concentration detector 30 and the processor 40. The ion membrane electrolytic cell 10 can further comprise the hydrogen tube 102 which is set between the cathode chamber 14 and the atomized/volatile gas mixing tank 60 to help the cathode chamber 14 input the hydrogen mixed gas into the atomized/volatile gas mixing tank 60. Because the structure of ion membrane electrolytic cell 10 and the gas pump 20 are mentioned above, they will not be elaborated herein. The hydrogen concentration detector 30 can be connected with the hydrogen tube 102 connected with the cathode chamber 14 to detect the concentration of hydrogen in the cathode chamber 14, and the processor 40 can respectively be connected with the hydrogen concentration detector 30 and the ion membrane electrolytic cell 10. Wherein the hydrogen mixed gas is generated by operating the gas pump 20 to input air from the outside into the cathode chamber 14 to decrease the concentration of hydrogen in the cathode chamber 14, or introducing the filtered gas filtered by the gas filter 26 into the cathode chamber 14 to decrease the concentration of hydrogen in the cathode chamber 14. When the hydrogen concentration detector 30 detects the concentration of hydrogen is higher than the predetermined value, the alarm signal is generated, and the operation of the ion membrane electrolytic cell 10 is stopped after the processor 40 receives the alarm signal and generates the stop signal to avoid the gas explosion caused by hydrogen with high concentration and improve the security. The predetermined value can be 3.5%, which is the gas volume concentration of hydrogen in the hydrogen mixed gas. The alarm signal is generated when the detected concentration is higher than the predetermined value. The predetermined value is not limited to it; it can be 4% or any other values according to the requirement of users.

The gas generator 1 can further comprise a gas-water separator 50 for separating the gas from the liquid. In an embodiment, the gas-water separator 50 is set between the ion membrane electrolytic cell 10 and the atomized/volatile gas mixing tank 60. The ion membrane electrolytic cell 10 can further comprise the hydrogen tube 102 connected with the cathode chamber 14 to output the hydrogen in the cathode chamber 14. The gas-water separator 50 can receive the hydrogen and separate the water from the hydrogen. In the embodiment, the atomized/volatile gas mixing tank 60 receives the hydrogen which is separated with water and generates atomized gas mixing with the hydrogen to form the healthy gas. Please refer to FIG. 3A. In the embodiment, the hydrogen tube 102 penetrates through the cathode collector plate 152 to connect the cathode chamber 14 with the outside; only the location of the hydrogen tube 102 and the connected method of the cathode chamber 14 are not limited to the diagram shown in FIG. 3A. The hydrogen tube 102 can be set on the ion exchange membrane 12, and the connected method can be any method which can connect the cathode chamber 14 with the outside. In an embodiment, the gas-water separator 50 can comprise the water return tube 52 and the gas outlet tube 54. The gas-water separator 50 can separate water from the hydrogen and receive hydrogen by connecting the cathode chamber 14 by the hydrogen tube 102. The water is outputted from the water return tube 52, and the hydrogen separated with water is outputted by the gas outlet tube 54. In the embodiment, the atomized/volatile gas mixing tank 60 can be connected with the gas-water separator 50 by the gas outlet tube 54 to receive the hydrogen separated with the water and generate the atomized gas mixing with hydrogen to form the healthy gas.

The gas generator 1 can further comprise the hydrogen concentration detector 30 and the processor 40. In an embodiment, the hydrogen concentration detector 30 can be connected with the gas-water separator 50 and detect the concentration of hydrogen in the hydrogen which is separated with water by the gas-water separator 50. The processor 40 can be respectively connected with the hydrogen concentration detector 30 and the ion membrane electrolytic cell 10. In an embodiment, the gas-water separator 50 comprises the gas outlet tube 54, and the hydrogen concentration detector 30 can connect with the gas outlet tube 54 and detect the concentration of hydrogen in the hydrogen separated with water by the gas-water separator and outputted by the gas outlet tube 54. The processor 40 can be respectively connected with the hydrogen concentration detector 30 and the ion membrane electrolytic cell 10. Wherein the hydrogen can be the hydrogen generated by electrolyzing water by the ion membrane electrolytic cell 10. When the hydrogen concentration detector 30 detects that the concentration of hydrogen in the hydrogen separated with water is higher than the predetermined value, the alarm signal is generated, wherein the predetermined value can be adjusted according to the requirement of users. When the processor 40 receives the alarm signal, the stop signal is generated to stop the operation of the ion membrane electrolytic cell 10 to avoid the gas explosion caused by the high concentration of hydrogen and improve the security. In an embodiment, the ion membrane electrolytic cell 10 is set between the gas-water separator 50 and the gas pump 20. The ion membrane electrolytic cell 10 can be connected with the gas-water separator 50 by the hydrogen tube 102, wherein the hydrogen tube 102 is connected with the cathode chamber 14. The ion membrane electrolytic cell 10 inputs hydrogen generated by the cathode chamber 14 into the gas-water separator 50. In an embodiment, by operating the pump 24, the gas suction tube receives the gas and inputs the gas into the cathode chamber 14 to decrease the concentration of hydrogen in the cathode chamber to generate the hydrogen mixed gas. The gas-water separator 50 receives the hydrogen mixed gas outputted from the hydrogen tube 102 and separates the water from the hydrogen mixed gas. The water is separated and outputted from the water return tube 52. The gas outlet tube 54 output the hydrogen mixed gas which is separated with the water. The hydrogen mixed gas can be generated by operating the gas pump 20 to input air from the outside into the cathode chamber 14 to decrease the concentration of hydrogen in the cathode chamber 14 or input the filtered gas filtered by the gas filter 26 into the cathode chamber 14 to decrease the concentration of hydrogen in the cathode chamber 14. In the embodiment, the atomized/volatile gas mixing tank 60 can be connected with the gas-water separator 50 by the gas outlet tube 54 to receive the hydrogen which is mixed the gas and separated with water and mixed with the atomized gas to form the healthy gas for the user to inhale.

In an embodiment, the hydrogen concentration detector 30 can be connected with the gas outlet tube 54. The hydrogen concentration detector 30 can detect the concentration of hydrogen in the hydrogen mixed gas which is separated with water by the gas-water separator 50. The processor 40 can be respectively connected with the hydrogen concentration detector 30 and the ion membrane electrolytic cell 10. Wherein the hydrogen mixed gas can be inputted the cathode chamber 14 by operating the gas pump 20 to decrease the concentration of hydrogen in the cathode chamber 14 to generate the hydrogen mixed gas. Or the filtered gas filtered by the gas filter 26 can be inputted the cathode chamber 14 to decrease the concentration of hydrogen in the cathode chamber 14 to generate the hydrogen mixed gas. When concentration of hydrogen in the hydrogen mixed gas which is separated with water detected by the hydrogen concentration detector 30 is higher than the predetermined value, the alarm signal is generated. Wherein, the predetermined value can be adjusted according to the requirement of users. When the processor 40 receives the alarm signal, the stop signal is generated to stop the operation of the ion membrane electrolytic cell 10 to avoid the gas explosion caused by hydrogen with high concentration. The predetermined value can be 3.5%, which is the gas volume concentration of hydrogen in the hydrogen mixed gas separated with the water by the gas-water separator 50. When the detected concentration is higher than the predetermined value, the alarm signal is generated. However, the predetermined value is not limited to it; the predetermined value can be 4%, 19% or any other values between 4% and 19% according to the requirement of users.

The gas generator 1 can further comprise a water tank 70. The ion membrane electrolytic cell 10 can further comprise a water admission tube 104 to recharge water from the outside into the cathode chamber 14 and the anode chamber 16. The water tank 70 can be connected with the ion membrane electrolytic cell 10 by the water admission tube 104 to recharge water in the water tank 70 into the anode chamber 16 and the cathode chamber 14. Please refer to FIG. 3A; in an embodiment, the water admission tube 104 penetrates through the anode collector plate 172 to connect the anode chamber 16 with the outside to recharge the water from the outside into the anode chamber 16 through the water admission tube 104. The water in the anode chamber 16 can penetrate the cathode chamber 14 through the ion membrane. Besides, the location of the gas tube can be set under the ion membrane 12, like FIG. 2 and FIG. 5, or any structure connecting the ion membrane electrolytic cell 10 and the outside. In another embodiment, the ion membrane electrolytic cell 10 can comprise two water admission tubes 104 which respectively connect the anode chamber 16 with the outside and the cathode chamber 14 with the outside to recharge water into the anode chamber 16 and the cathode chamber 14.

In an embodiment, the gas-water separator 50 can be connected with the water tank 70 by the water return tube 52. The gas-water separator 50 can separate water from hydrogen or the hydrogen mixed gas. The water which is separated from hydrogen or the hydrogen mixed gas is outputted from and inputted into the water tank 70 to recharge to the ion membrane electrolytic cell 10 to form a water cycle.

The ion membrane electrolytic cell 10 can further comprise an oxygen tube 106 which is connected with the anode chamber 16 to output oxygen to the outside. In an embodiment, the ion membrane electrolytic cell 10 can be connected with the water tank 70 by the oxygen tube 106 to input oxygen generated by the anode chamber 16 into the water tank 70 through the oxygen tube 106 and outputted from the water tank 70. Please refer to FIG. 3A; in an embodiment, the oxygen tube 106 penetrates through the anode collector plate 172 to connect the anode chamber 16 with the outside to output oxygen generated by the anode chamber 16 through the oxygen tube 106. The location of the oxygen tube 106 and the connected method of the anode chamber 16 are not limited to the diagram of FIG. 3. The oxygen tube 106 can be set on the ion exchange membrane 12 like FIG. 2 and FIG. 5 or any structure which can connect the anode chamber 16 with the outside.

The water tank 70 can accommodate water. Please refer to FIG. 5; in an embodiment, the water tank 70 can further comprise a water inlet opening 72 for recharging water into the water tank 70.

In an embodiment, please refer to FIG. 5, the water in the water tank 70 is maintained at a water level. The water tank 70 can further comprise a water level control valve which can control the water level of the water in the water tank 70. In an embodiment, the water level control element can be a water outlet valve 74. When the water level is higher than a predetermined water level, part of the water in the water tank 70 is released from the water tank 70. The water level control element is not limited to the water outlet valve 74. The water level control element can be any element which can control the water level.

In another embodiment, please refer to FIG. 5; the gas generator 1 can comprise an ion membrane electrolytic cell 10 and the gas pump 20. The ion membrane electrolytic cell 10 is connected with the gas pump 20. The ion membrane electrolytic cell 10 inputs air from the outside into the cathode chamber 14 of the ion membrane electrolytic cell 10 by operating the gas pump 20 to decrease the concentration of hydrogen in the cathode chamber 14 and generate the hydrogen mixed gas. The ion membrane electrolytic cell 10 is mentioned above, so it will not be elaborated herein.

The ion membrane electrolytic cell 10 comprises the gas tube 100 connecting the cathode chamber 14 with the outside. Please refer to FIG. 3A; in an embodiment, the gas tube 100 penetrates through the cathode collector plate 152 to connect the cathode chamber 14 with the outside. The location of the gas tube 100 and the connected method of the cathode chamber 14 is not limited to the diagram mentioned. The gas tube 100 can be set under the ion exchange membrane 12 shown in FIG. 2 and FIG. 5 or any other place where can let the gas tube 100 connect the cathode chamber 14 with the outside. The gas pump 20 receives air and input air into the cathode chamber by the gas tube to decrease the concentration of hydrogen in the cathode chamber and generate a hydrogen mixed gas. In an embodiment, the gas pump 20 comprises a gas suction tube 22 and a pump 24. The gas suction tube 22 is connected with the outside to receive air from the outside. The pump 24 is set between the gas suction tube 22 and the gas tube 100. The pump 24 can be connected with the cathode chamber 14 of the ion membrane electrolytic cell 10 by the gas tube 100. The gas suction tube 22 can receive the gas from the outside and input the gas from the outside into the cathode chamber 14 by operating the pump 24 to decrease the concentration of hydrogen in the cathode chamber 14 and generate a hydrogen mixed gas. The gas volume concentration of hydrogen in the hydrogen mixed gas is lower than 3.5%, which can avoid the gas explosion and improve the security by outputting the hydrogen with low concentration from the ion membrane electrolytic cell 10. However, the gas volume concentration is not limited to it. The concentration of hydrogen can be adjusted according to the requirements of users.

In an embodiment, the gas pump 20 can further comprise a gas filter 26 for filtering the gas from the outside. The gas filter 26 is connected with the pump 24 by the gas suction tube 22. The gas suction tube 22 can receive the filtered gas filtered by the gas filter 26 by operating the pump 24. The gas suction tube also can help input the filtered gas into the cathode chamber 14 to decrease the concentration of hydrogen in the cathode chamber 14 and form the hydrogen mixed gas.

The gas generator 1 can further comprise a hydrogen concentration detector 30 and the processor 40. The ion membrane electrolytic cell 10 can further comprise a hydrogen tube 102 which is set between the cathode chamber 14 and the atomized/volatile gas mixing tank 60 to input the hydrogen mixed gas from the cathode chamber 14 into the atomized/volatile gas mixing tank 60. Because the structure of the ion membrane electrolytic cell 10 and the gas pump 20 is mentioned above, it will not be elaborated here. The hydrogen concentration detector 30 can be connected with the hydrogen tube 102 connected with the cathode chamber 14 to detect the concentration of hydrogen of the hydrogen mixed gas in the cathode chamber 14. The processor 40 can respectively connect with the hydrogen concentration detector 30 and the ion membrane electrolytic cell 10. Wherein the hydrogen mixed gas can be the hydrogen mixed gas in the cathode chamber 14 generating by mixing the gas from the outside and hydrogen by operating the gas pump 20. The hydrogen mixed gas also can be generated from the gas which is filtered by the gas filter 26 and inputted into the cathode chamber 14 to decrease the concentration of hydrogen. When the hydrogen concentration detector 30 detects that the concentration of hydrogen is higher than the predetermined value, the alarm signal is generated. The stop signal is generated when the processor 40 receives the alarm signal to stop the operation of the ion membrane electrolytic cell 10 to avoid the gas explosion made by the high concentration of hydrogen and improve the security as well. The predetermined value mentioned above is 3.5%, which is the gas volume concentration of hydrogen in the hydrogen mixed gas. When the concentration is higher than the predetermined value, the alarm signal is generated. However, the predetermined value is not limited to it; the predetermined value can be 4% or any other values. Namely, the predetermined value is adjustable, and the predetermined value can be adjusted depending on the needs of the user.

To summarize, the ion membrane electrolytic cell 10 of the gas generator 1 can solves the problems that the familiar basic cell has. The problems are the corrosion of the tank, environmental pollution and the chance to inhale the gas with electrolyte because the filter has some problems. The gas generator 1 of the present invention can decrease the concentration of hydrogen in the cathode chamber 14 by receiving the gas from the outside to decrease the possibility of gas explosion caused by hydrogen with high concentration and then improve the security. The gas generator 1 of this embodiment of the present invention can separate water from hydrogen or the hydrogen mixed gas and input hydrogen which is separated with water into the water tank 70. The water in the water tank 70 can be recharged to the ion membrane electrolytic cell 10 to generate the water cycle.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A gas generator, comprising:
    a water tank, configured to accommodate water;
    an ion membrane electrolytic cell comprising an ion exchange membrane, a hydrogen tube, an oxygen tube, a water admission tube, a cathode chamber, an anode chamber, and two fins configured on the outside of the ion membrane electrolytic cell, an anode electrode set in the anode chamber and a cathode electrode set in the cathode chamber, the ion exchange membrane set between the cathode chamber and the anode chamber, wherein oxygen is generated by the anode electrode and hydrogen is generated by the cathode electrode when water is electrolyzed by the ion membrane electrolytic cell, the oxygen tube is separated from the water admission tube, both the oxygen tube and the water admission tube are directly connected with the water tank, and the oxygen tube outputs the oxygen into the water tank and the water admission tube receives water from the water tank, the two fins respectively forms a plurality of hollow portions thereon, and the hydrogen tube, the oxygen tube, the water admission tube penetrate through the hollow portions when the ion membrane electrolytic cell is assembled; and
    an atomized/volatile gas mixing tank coupled to the ion membrane electrolytic cell for receiving the hydrogen and generating an atomized gas mixed with the hydrogen to form a healthy gas, wherein the atomized gas is selected from a group consisting of volatile oil, vaporized medicinal liquid, water vapor and a combination thereof;
    wherein the oxygen generated by the ion membrane electrolytic cell keeps separated from the atomized gas and the hydrogen.

2. The gas generator of claim 1, further comprising a gas-water separator coupled to the ion membrane electrolytic cell and the atomized/volatile gas mixing tank for receiving the hydrogen, separating the water from the hydrogen, and then outputting the hydrogen separated from the water to the atomized/volatile gas mixing tank.

* * * * *